United States Patent [19]

Blichare et al.

[11] 4,132,753

[45] Jan. 2, 1979

[54] PROCESS OF PREPARING ORAL SUSTAINED RELEASE GRANULES

[75] Inventors: Mitchell S. Blichare, Blauvelt; Gerald J. Jackson, Jr., Berdonia, both of N.Y.

[73] Assignee: American Cyanamid Company, Stamford, Conn.

[21] Appl. No.: 687,070

[22] Filed: Nov. 3, 1967

Related U.S. Application Data

[63] Continuation of Ser. No. 432,288, Feb. 12, 1965, abandoned.

[51] Int. Cl.$^2$ .............................................. B01J 2/12
[52] U.S. Cl. .................................. 264/25; 264/117; 264/122; 424/19; 424/38

[58] Field of Search ................... 264/117, 122, 25; 167/82, 82.9; 424/19, 38

[56] References Cited

U.S. PATENT DOCUMENTS

| 3,206,528 | 9/1965 | Coombs et al. | 264/117 |
| 3,244,132 | 1/1967 | Dougherty | 264/117 |
| 3,279,998 | 10/1966 | Raff et al. | 424/19 |

Primary Examiner—Robert F. White
Assistant Examiner—James R. Hall
Attorney, Agent, or Firm—Claude J. Caroli

[57] ABSTRACT

This disclosure relates to the process of preparing granules of controlled release medicament by continually agitating a mixture of powdered medicament and finely divided wax-like material while subjecting the mixture to radiation heating.

16 Claims, 1 Drawing Figure

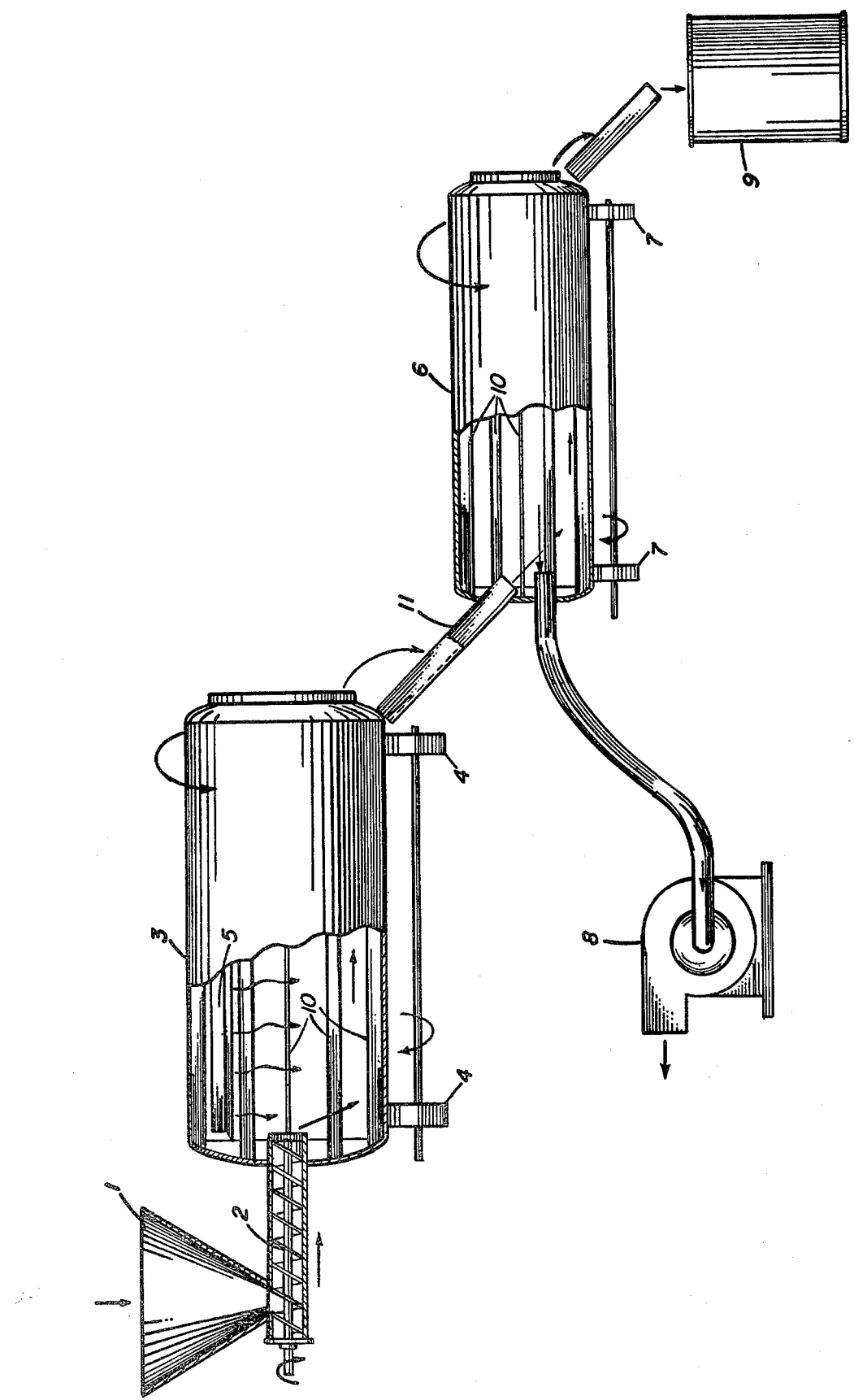

PROCESS OF PREPARING ORAL SUSTAINED RELEASE GRANULES

This application is a continuation of Ser. No. 432,288 filed Feb. 12, 1965.

This invention relates to a novel process for preparing sustained release medicament granules.

Sustained release medications are receiving more and more attention in recent years. They have the advantages of more uniform and prolonged therapeutic blood levels of the medicament, convenience to the patient who has to take medication at shorter intervals and gradual release of the medicament which may otherwise be irritating to the gastrointestinal tract if administered in immediately available therapeutic doses.

A number of methods have been developed in the pharmaceutical industry to achieve this result. For example, the medicament may be loaded on an inert seed of uniform size and the seeds then coated with various amounts of fatty, plastic or waxy material. Blending then effects the desired release pattern. Another way is to prepare granules of differing sizes by conventional methods and coating to a single wax, fat or plastic level. The release varies with the particle size and so a sustained action can be obtained. Another method is to disperse the medicament in a wax, plastic or fat matrix, commuting and compressing it into tablets. The drug in this case is slowly leached from the relatively insoluble matrix. It has also been proposed to absorb the therapeutic agent on ion exchange resins which release it slowly in the gastrointestinal juices. Finally, another method is to mix synthetic or natural hydrophilic gums with the medicament and compress the mixture into tablets. These gums cause the tablet to swell when in an aqueous medium and the hydrated gum is a water resistant barrier.

All of the above techniques, though effective, require frequent handling or other time consuming operations and increases the cost of sustained release medication. Also in the normal processes, the wax, fat or other plastic material is dissolved and the solvents are lost in the processing which results in a further increase in cost.

The present invention produces granules of pharmaceutically active medicaments which release slowly. Throughout the specification and claims the wax, fat or plastic substance will be referred to as a wax-like material. The present invention preferably involves finely divided wax-like material of a considerably smaller average size than that of the final granules. The wax-like material is contacted with powdered medicament at a higher temperature, preferably at a temperature somewhat above the melting point of the wax-like material. Constant agitation is maintained and the powdered medicament sinks into the molten surface of the wax-like material pieces. The granules thus formed can then be tabletted, if necessary with the addition of conventional tabletting lubricants or encapsulated. Products are obtained which release the medicament at predetermined rates. The optimal proportion of wax used when the granules are to be tabletted is considerably smaller than when the granules are to be filled into capsules. The method by which the temperature of the powder is brought to and maintained slightly above the melting point of the waxlike material may vary. Auxiliary heating as for example by radiant heat is almost always necessary to prevent excessively rapid cooling off of the materials.

One satisfactory method of performing the present invention is to preheat the powder, either by radiation or conduction or both and then mix it with a wax-like material which latter may be, and preferably is, warmed to a temperature a little below its melting point. The powder, of course, is heated to a temperature above the melting point and mixing, for example in a conventional coating pan, can then be effected with maintenance of gentle heating, preferably from infrared sources, to prevent too rapid cooling off.

Another method of carrying out the present invention is to mix the powder and the wax-like material and then to heat both by radiation. The powder is almost always opaque to infrared radiation whereas the wax-like material may be more or less transparent at least over considerable wave length ranges. As a result the powder heats up more rapidly and to a higher temperature, for example from 6 to 8° C. above the temperature reached by the wax-like material. The heating should be regulated so that the wax-like material does not actually melt but is brought up to a temperature only slightly below its melting point so that the hotter powder sinks into the pieces of wax-like material as is the case in the first method where the powder is preheated before admixture.

Reference has been made to the particular use of the present invention and its products, for the controlled release of medicaments. This is the most important single field and is normally thought of as releasing the medicament over a fairly long period of time which may be measured in hours after ingestion of the tablet or other product containing the granules. It should be noted that the controlled release feature does not have to be a controlled release over a long period of time. Thus, for example, the wax-like material may be fairly readily soluble in the gastric juices and so the releasing rate, although still controlled may take only minutes instead of hours. Each case has a predetermined controlled release rate effected which is the important factor.

While the process aspect of the present invention, is in many ways, the more important it should be understood that the present invention also results in the production of a new type of granule in which the powder has penetrated in from the surface rather than the wax-like material being coated on the powder. This characteristic is what results in the improved accuracy of control of time of release of the powder after ingestion of the tablet or other form in which the granules are administered. Therefore in another aspect of the invention the new product constitutes a part of the present invention.

The choice of the wax-like material depends on several factors. One is its physical properties in the finished granule and the other is its melting point. The latter characteristic in some cases may be of predominant importance where medicaments are to be used which are sensitive to high temperatures. In such case, relatively lower melting wax-like material should be used so that the preheating of the medicament to temperatures somewhat above the melting point of the wax-like material will not subject the medicament to temperatures at which it is adversely effected. Wax-like materials having melting points ranging from about 30° C. up to as much as about 100° C. may be used, the latter, of course, being useable only with medicaments which can stand the higher temperature. Even when the temperature sensitivity of the medicament is not the controlling factor, the choice of wax-like material may be dictated by different considerations. For example, if very low melting material is used, granules, whether tabletted or not, may tend to soften in a warm room and stick together. Also if the final product is shipped, they are sometimes exposed to considerably elevated temperatures in transit. Another factor is that as a general thing the low melting wax-like materials also form softer final products and so a choice should be made which will give the physical characteristics of the final product that are optimum for a particular use.

Among a number of wax-like materials which can be used are the following:

glyceryl monostearate (m.p. 58° C.)
hydrogenated tallow (m.p. 46° C.)
castor wax (m.p. 86-88° C.)
myristyl alcohol (m.p. 38° C.)
white beeswax (m.p. 62°-65° C.)
myristic acid (m.p. 54° C.)
stearyl alcohol (m.p. 56°-60° C.)
substituted monoglycerides
substituted diglycerides
substituted triglycerides
carnauba wax (m.p. 82°-84° C.)
acetylated monoglycerides (m.p. 41°-43° C.)
stearic acid (m.p. 69°-70° C.)

It should be understood that it is in no sense necessary to use only a single wax-like material. Mixtures may be employed and in some cases this is quite desirable. For example, carnauba wax imparts a desirable hardness to the final product. However if carnauba wax is used alone its high melting point, over 80° C. may be undesirable either because of a heat sensitive medicament or the greater difficulty of maintaining the proper differential in temperature between the powder and the wax-like material at the higher temperatures or both. In such cases a small amount of carnauba wax may be combined with a lower melting wax, for example glyceryl monostearate, to impart additional hardness to the final product without raising the overall melting point of the mixture to an inconveniently high value. The listed types of wax-like material are not intended to limit the present invention but merely to serve as typical illustrative examples. However, this is not to say that for all purposes a particular wax-like material is not the best. In general it has been found that for most products the monoglycerides such as glyceryl monostearate have many advantages and this class of material may therefore be considered as the preferred one for most products under the present invention.

Reference has been made above to tabletting the granules and for many purposes this is a very desirable form in which to market the products of the present invention which, however, is not limited to such form and so will be broadly claimed in terms of granules regardless of whether they are then tabletted, incorporated in gelatin capsules or otherwise packaged. Since the present invention ends when the granules have been formed, it is not intended to limit it to any particular marketing form even though, as pointed out above, for many purposes the tablet form is preferred.

The wax-like substances referred to above are for sustained release products because they are relatively insoluble in gastric juices. If a controlled release product is desired which releases much more quickly, although still at the controlled rate, such water soluble or dispersible products as wax-like polyethylene glycol or other polyglycols may be used. The melting point of such products, of course, depends on the molecular weight of the polymer used. As far as the present invention is concerned, the process proceeds in the same manner regardless of whether the wax-like material is relatively soluble or insoluble in gastric juices.

Except for the consideration of sensitivity to temperature which has been set out above the present process is useful with practically any powdered medicament or mixtures of medicaments. Of course, if the mixture is used the choice of wax-like material which determines the temperature conditions of the process must be suitable for the most temperature sensitive constituent of the mixture. Among typical drugs are phenobarbital, meprobamate, d-amphetamine sulfate, ferrous fumarate, tridihexethyl chloride and acetazolamide.

One of the important physical characteristics of the granules of the present invention is that when reasonable care is taken to maintain agitation during the admixture, the granules are spherical in shape. This lends itself to considerable uniformity in release characteristics and also makes the granules very suitable for tabletting because the spheres are free flowing and so are easily used in high output tabletting equipment.

While broadly the present invention is not limited to any particular equipment in which the process is carried out or whether the process is a batch process or a continuous one in a more specific aspect of the invention an improved continuous process and improved apparatus is included. For smaller batches the conventional rotating tablet coating pan may be used and where the batch size and properties of the materials are suitable this is an excellent process. However for large scale commercial processes difficulties are sometimes encountered because, while the process operates with practically any material with smaller coating pans, for example eight inch pans, when it is attempted to scale up the batches, very large coating pans sometimes do not give optimum results. The granules are not evenly spherical, uniform heating is more difficult, rapid cooling is difficult, and, or course, any batch process involves more labor than does a continuous automated or semiautomated process.

Many of the specific examples to follow will be described in conjunction with smaller batches for which coating pans are suitable. However, in a more specific aspect of the present invention, a continuous process and apparatus is preferred. In this process the materials, that is to say powder and wax-like materials, are introduced into a rotating tumbling cylinder which is provided with an infrared heater, capable of adjustment, which gives the desired amount of heating for a particular material. Very large throughputs are obtainable in comparison to that practical with smaller coating pans and a high degree of uniformity is made possible once the continuous process has been adjusted with regard to throughput, radiation heat input, and the like. Therefore, the continuous process is preferred. However, in illustrating the invention only two examples of the continuous process are given, it being understood that this process is equally useable with the materials described in the batch examples. An additional advantage of the continuous process is that average granule size can be varied by varying the time of residence in the heated portion of the apparatus.

It is an advantage of the preferred continuous process and apparatus that it is normally not necessary to preheat the powder or the wax-like material or both. While this is also not necessary in every case in a batch process the continuous process lends itself particularly to the elimination of the preheating. Another advantage of the continuous process is that it is possible to discharge granules which are fully formed at temperatures somewhat higher than the melting point of the wax-like material and this temperature is not as critical as it is with batch processes where the agitation may be less violent or less continued. Even in a continuous process temperature conditions must be maintained within limits so that the granules do not stick together. However, the temperature ranges are broader and control is easier in the continuous process and thus constitutes one of the practical operating advantages.

The invention will be descibed in greater detail in conjunction with the drawings which illustrate, in diagrammatic form typical apparatus for carrying out the continuous process modification of the present invention.

The invention will also be described in greater detail in conjunction with specific examples. In each case where controlled release rates are indicated they were obtained with artificial gastric and/or intestinal juices to eliminate any nonuniformity.

EXAMPLE 1

800 grams of ferrous fumarate powder was mixed with 200 grams of powdered glyceryl monostearate and transferred to an 8 inch coating pan. The pan was rotated, tumbling the mixture and it was heated by an infrared lamp until the mixture reached 64°–66° C. The powder was hotter by at least 7° C. The waxy material melted, absorbed the powder and formed spherical granules which were sieved to pass through a 12 mesh screen and be retained on a 60 mesh screen. Thereafter they were lubricated with one-half percent magnesium stearate. The following assays were obtained:
Iron potency = 24.6%
Release Rate:
1 Hour = 45.7%
2 Hours = 76.7%
4 Hours = 98.6%

EXAMPLE 2

1345 grams of ferrous fumarate powder was heated to 90° C. in an 18 inch electrically heated tablet coating pan. The pan was rotated and while the powder was tumbling, 335 g. of powdered glyceryl monostearate was rapidly added. The temperature dropped to 59–60° C. and heat was applied from an infrared lamp raising the temperature to about 65° C. A current of air at room temperature was then blown into the rotating granules for 5 minutes and the granules were allowed to cool to room temperature while rotating. They were then sieved through a 12 mesh screen and onto a 40 mesh screen and lubricated with one-half percent magnesium stearate. The following assays were obtained:
Iron potency = 25.83%
Release Rate:
1 Hour = 49.7%
2 Hours = 77.8%
4 Hours = 96.2%

EXAMPLE 3

200 grams of phenobarbital powder was mixed with 60 grams of powdered glyceryl monostearate and 2 grams of magnesium stearate. The mix was then transferred to an 8 inch coating pan, tumbled and heated with an infrared lamp to 58.5° C. The granules were formed and allowed to cool to room temperature and the material sieved through a 12 mesh screen and onto a 40 mesh screen and lubricated with a one-half percent magnesium stearate. The following assays were obtained:
Potency = 74.4%
Release Rate:
½ Hour = 19.3%
2 Hours = 42.2%
4½ Hours = 85.1%
7 Hours = 94.1%
The release rate assay was performed in artificial gastric fluid for the first two hours and in artificial intestinal fluid for the remaining time.

EXAMPLE 4

400 grams of phenobarbital powder was mixed with 12 grams of magnesium stearate and transferred into an 8 inch coating pan. The powder was tumbled and heated to 87° C. with an infrared lamp. While tumbling, 100 grams of powdered glyceryl monostearate was rapidly added, the temperature dropping to 56° C. Tumbling and infrared heating was maintained until the temperature rose to 65° C. and the granules were then allowed to cool to room temperature. The product was sieved through 14 mesh and on to 40 mesh and lubricated with one-half percent of magnesium stearate. The following assays were obtained:
Potency = 74.77%
Release Rate:
½ Hour = 15.6%
2 Hours = 39.4%
4½ Hours = 83.3%
7 Hours = 94.1%

EXAMPLE 5

200 grams of acetazolamide was mixed with 50 grams of powdered glyceryl monostearate and 7.5 grams of magnesium stearate. The mixture was transferred to an 8 inch coating pan and heated while tumbling with an infrared lamp to 63° C. The granules were then allowed to cool to room temperature and sieved through 12 mesh and onto 40 mesh. The following assays were made:
Potency = 73.95%
Release Rate:
] Hour = 30.2%
2 Hours = 51.3%
4½ Hours = 97.1%
7 Hours = 100.0%

EXAMPLE 6

400 grams of acetazolamide was mixed with 12 grams of magnesium stearate transferred to an 8 inch coating pan. While tumbling the powder was heated to 85° C. with an infrared lamp and then 100 grams of powdered glyceryl monostearate rapidly added. The temperature dropped to 54° C. and was then raised to 64° C. with an infrared lamp whereupon the granules were allowed to cool to room temperature while tumbling. The material was sieved through a 14 and onto a 40 mesh screen and lubricated with one-half percent magnesium stearate. The following assays were obtained:
Potency = 73.49%
Release Rate:
½ Hour = 22.8%
2 Hours = 42.9%
4½ Hours = 91.5%
7 Hours = 99.0%

EXAMPLE 7

200 grams of meprobamate powder was mixed with 50 grams of powdered glyceryl monostearate and 6 grams of magnesium stearate. The mixture was transferred to an 8 inch coating pan and heated while tumbling with an infrared lamp to 60° C. The granules were allowed to cool to room temperature and the material sieved through 12 mesh onto 40 mesh and lubricated with one-half percent magnesium stearate. The following assays were obtained:
Potency = 67.55%
Release Rate:
½ Hour = 67.4%
2 Hours = 93.7%
4½ Hours = 99.4%
7 Hours = 99.9%

EXAMPLE 8

200 grams of meprobamate powder was mixed with 50 grams of granular hydrogenated tallow and 6 grams of magnesium stearate. The mixture was transferred to an 8 inch coating pan and heated while tumbling to 56° C. with an infrared lamp. The granules were then allowed to cool to room temperature and sieved on 40 mesh screen, the coarser material being retained. It was then lubricated with one-half percent magnesium stearate and the following assays were obtained:
Potency = 65.81%
Release Rate:
½ Hour = 38.6%
2 Hours = 71.6%
4½ Hours = 93.9%
7 Hours = 98.3%

EXAMPLE 9

200 grams of meprobamate powder was mixed with 6 grams of magnesium stearate and transferred to an 8 inch coating pan. While tumbling the powder was heated to 65° C. with an infrared lamp. Thereupon 50 grams of granular hydrogenated tallow was rapidly added, the temperature dropping to 53° C. Tumbling was continued until the temperature rose to 56° C. and the granules were then allowed to cool to room temperature. The material retained on a 40 mesh screen was then lubricated with one-half percent magnesium stearate and the following assays were obtained:
Potency = 67.75%
Release Rate:
½ Hour = 55.3%
2 Hours = 58.4%
4½ Hours = 100%

EXAMPLE 10

200 grams of acetazolamide powder was mixed with 6 grams of magnesium stearate and 50 grams of granular myristyl alcohol. The mixture was transferred to an 8 inch coating pan and heated with an infrared lamp while tumbling to 38° C. The granules which formed were allowed to cool to room temperature and were then lubricated with 2.5 grams of magnesium stearate. The material on a 40 mesh screen assayed as follows:
Potency = 71.41%
Release Rate:
½ Hour = 32.3%
2 Hours = 50.9%
4½ Hours = 95.3%
7 Hours = 97.6%

EXAMPLE 11

200 grams of acetazolamide powder was mixed with 6 grams of magnesium stearate and transferred to an 8 inch coating pan. The powder was heated with an infrared lamp to 100° C. while tumbling and 50 grams of granular carnauba wax which had been preheated to 70° C. was added. The temperature of the mixture dropped to 75° C. and heating with the infrared lamp was continued until it rose again to 83° C. The granules which formed were allowed to cool to room temperatue while tumbling, and then lubricated with 2.5 grams of magnesium stearate. The material passing through a 12 mesh screen and retained on a 40 mesh screen assayed as follows:
Potency = 71.0%
Release Rate:
½ Hour = 21.6%
2 Hours = 33.2%
4½ Hours = 73.2%
7 Hours = 86.5%

EXAMPLE 12

200 grams of acetazalamide powder was mixed with 6 grams of magnesium stearate and transferred to an 8 inch coating pan. The powder was heated while tumbling with an infrared lamp to 95° C. and 50 grams of granualr hydrogenated lard having a melting point of about 68° C. and sold under the name Myverol by the Distillation Products Industries of Rochester, New York, was added. The temperature of the mixture dropped to 65° C. and the infrared heating was continued until it rose again to 70° C. The granules formed were allowed to cool to room temperature while tumbling and then lubricated with 2.5 grams of magnesium stearate. The material retained on a 40 mesh screen assayed as follows:
Potency = 72.1%
Release Rate:
½ Hour = 32.1%
2 Hours = 47.6%
4½ Hours = 89.6%
7 Hours = 96.8%

EXAMPLE 13

200 grams of acetazolamide powder was mixed with 6 grams of magnesium stearate, transferred to an 8 inch coating pan. The powder was then heated with an infrared lamp to 90° C. While tumbling and then 50 grams of granular stearic acid was added. The temperature of the mixture dropped to 50° C. and the infrared heating was maintained until the temperature rose to 65° C. The granules which formed were allowed to cool to room temperature while tumbling and then lubricated to 2.5 grams of magnesium stearate. The product was sieved through a 12 mesh and onto a 40 mesh screen and assayed as follows:
Potency = 75.5%
Release Rate:
½ Hour = 15.1%
2 Hours = 36.4%
4½ Hours = 90.0%
7 Hours = 96.0%

EXAMPLE 14

A homogeneous mixture of 8 parts by weight of ferrous fumarate powder and 2 parts of glyceryl monostearate powder was prepared by tumbling for 10 minutes.

The glyceryl monostearate was sifted through a 16 mesh screen prior to tumbling in order to break up any soft lumps present. The powder mixture was then fed into the apparatus of the drawing by filling a hopper (1) and feeding by means of a screw (2) into an elongated rotating cylinder (3). This cylinder was rotated on rollers (4), the drive for which is not shown as this portion of the present invention does not depart from conventional practice for rotating kilns. The feed was 590 grams per minute and the cylinder, measuring 58 inches long by 11 inches in diameter with a 2 inch flange at the feed end, was rotated at 30 rpm. The baffles (10) picked up the powder and constantly agitated it. An infrared heater (5) of 2500 watt capacity was suspended in the cylinder. So that the heat source was 4 inches from the plane of the tumbling powders and radiation was perpendicular thereto. The infrared heating source was operated at a wattage such that a residence time of 17 minutes was maintained and the temperature of the pellets discharged from the other end of the cylinder was approximately 70° C. The adjustment of wattage of the infrared heater was by conventional means, (not shown) and required initial adjustment after which continuous running was maintained.

The throughput was 33 kilograms of granules per hour, the granules being discharged from the end of the cylinder into the chute (11), rolling down into a second rotating cylinder (6) turning on rollers (7) and provided with an exhaust system (8) to draw cool air through the cylinder so that the granules are cooled while agitated. The length of the cylinder (6), its inclination, and rotation were adjusted to permit a residence time comparable to that in cylinder (3).

Cooled pellets at substantially room temperature were discharged into a suitable container (9). About 3% of the granules were oversize, plus 12 mesh, and were removed by sieving. As the sieving forms no part of the apparatus of the present invention, it is not shown but can be incorporated between the cylinder (6) and the final container (9).

A screen analysis of the $-12$ mesh fraction was as follows:

12/14 mesh = 0.9%
14/20 = 22.2
20/30 = 42.5
30/40 = 16.7
40/60 = 4.5
$-60$ = 13.3

The granules were lubricated with 1% magnesium stearate giving the following medicament release rate:
Iron potency = 25.28%
Iron release rate = 1 hr. = 64.6
2 hr. = 87.9
4 hr. = 98.3

The above examples are illustrative of a continuous process in which no preheating of either the powder or the wax-like material was used. For many granulation processes under the present invention this is desirable as it simplifies operations. However, it should be understood that preheating one or both ingredients may be used. For example, if the continuous process is used with the carnauba wax as described for batch processes in Example 11 preheating is often desirable. When preheating is used the amount of radiation heating must be adjusted and it is, of course, possible to operate the equipment with greater throughputs as the time of residence in the cylinder need not be as long. Nevertheless where the nature of the ingredients permit, it is usually simpler to operate the modification without preheating.

What is claimed is:

1. A process of preparing granules of controlled release medicament which comprises: continuously agitating a mixture of (a) powdered medicament and (b) finely divided wax-like material having a melting point between about 30° C and 100° C, while subjecting the mixture to radiation heating at a temperature sufficiently high that the medicament powder has a temperature higher than the melting point of the wax-like material, the temperature of the medicament powder also being higher than the actual temperature of the wax-like material, whereby the hotter medicament powder sinks into the molten surfaces of the wax-like material to form granules comprising medicament powder and wax-like material; and cooling, lubricating, and sizing the resulting granules to sizes between about 12 and 60 mesh.

2. The process of claim 1 in which the finely divided wax-like material is selected from the group consisting of glyceryl monostearate, hydrogenated tallow, castor wax, myristyl alcohol, white beeswax, myristic acid, stearyl alcohol, substituted monoglycerides, substituted diglycerides, substituted triglycerides, carnauba wax, acetylated monoglycerides, stearic acid, polyethylene glycols and mixtures thereof.

3. The process of claim 2 in which the wax-like material is glyceryl monostearate.

4. The process of claim 2 in which the wax-like material is a hydrogenated fat.

5. The process of claim 2 in which the wax-like material is a waxy aliphatic alcohol.

6. The process of claim 1 in which the medicament is ferrous fumarate.

7. The process of claim 1 in which the medicament is meprobamate.

8. The process of claim 1 in which the medicament is phenobarbital.

9. The process of claim 1 in which the medicament is acetazolamide.

10. The process of claim 1 in which the medicament powder is preheated to a temperature above the melting point of the wax-like material, and the hot medicament powder is then mixed with the wax-like material.

11. The process of claim 10 in which the wax-like material is also preheated to a temperature above room temperature but below its melting temperature before it is mixed with the powdered medicament.

12. The process of claim 1 in which the powder and wax-like material are at substantially the same temperature when they are mixed, this temperature being below the melting point of the wax-like material, and in which the radiation heating of the mixture is continued until the temperature of the powder is at least 6-8° C above the melting point of the wax-like material.

13. A continuous process according to claim 1 in which the medicament and wax-like material are introduced into one end of a rotating tumbling cylinder and subjected to infrared radiation heating inside said cylinder for a period of time to form spherical granules at a final temperature above the melting point of the wax-like material but insufficiently high to cause the granules to adhere to each other while being tumbled; and the granules are dispersed into a second rotating cylinder having a cool air exhaust system and cooled therein to a temperature below the melting point of the waxlike material, while being maintained in a state of continuous agitation.

14. A continuous process according to claim 12 in which the medicament and wax-like material are introduced into one end of a rotating tumbling cylinder and subjected to infrared radiation heating inside said cylinder for a period of time to form spherical granules at a final temperature above the melting point of the wax-like material, but insufficiently high to cause the granules to adhere to each other while being tumbled; and the granules are dispersed into a second rotating cylinder having a cool air exhaust system and cooled therein to a temperature below the melting point of the wax-like material, while being maintained in a state of continuous agitation.

15. A continuous process according to claim 10 in which the medicament and wax-like material are introduced into one end of a rotating tumbling cylinder and subjected to infrared radiation heating inside said cylinder for a period of time to form spherical granules at a final temperature above the melting point of the wax-like material but insufficiently high to cause the granules to adhere to each other while being tumbled; and the granules are dispersed into a second rotating cylinder having a cool air exhaust system and cooled therein to a temperature below the melting point of the wax-like material, while being maintained in a state of continuous agitation.

16. A continuous process according to claim 11 in which the medicament and wax-like material are introduced into one end of a rotating tumbling cylinder and subjected to infrared radiation heating inside said cylinder for a period of time to form spherical granules at a final temperature above the melting point of the wax-like material but insufficiently high to cause the granules to adhere to each other while being tumbled; and the granules are dispersed into a second rotating cylinder having a cool air exhaust system and cooled therein to a temperature below the melting point of the wax-like material, while being maintained in a state of continuous agitation.

* * * * *